US011647817B2

(12) United States Patent
Hsu et al.

(10) Patent No.: US 11,647,817 B2
(45) Date of Patent: May 16, 2023

(54) WEARABLE ELECTRONIC DEVICE AND ASSEMBLING METHOD THEREOF

(71) Applicant: Acer Gadget Inc., Taipei (TW)

(72) Inventors: Yen-Ming Hsu, Taipei (TW); Pei-Wen Jung, Taipei (TW)

(73) Assignee: Acer Gadget Inc., Taipei (TW)

( * ) Notice: Subject to any disclaimer, the term of this patent is extended or adjusted under 35 U.S.C. 154(b) by 709 days.

(21) Appl. No.: 16/683,270

(22) Filed: Nov. 14, 2019

(65) Prior Publication Data

US 2021/0022461 A1 Jan. 28, 2021

(30) Foreign Application Priority Data

Jul. 25, 2019 (TW) ................. 108126422

(51) Int. Cl.
*A44C 23/00* (2006.01)
*A61M 37/00* (2006.01)
*G06M 1/27* (2006.01)

(52) U.S. Cl.
CPC ............. *A44C 23/00* (2013.01); *A61M 37/00* (2013.01); *G06M 1/27* (2013.01)

(58) Field of Classification Search
CPC .......... A44C 23/00; A61M 37/00; G06M 1/27
USPC ........................................................ 434/246
See application file for complete search history.

(56) References Cited

U.S. PATENT DOCUMENTS

| 6,296,364 | B1 | 10/2001 | Day et al. | |
| 10,314,496 | B2 * | 6/2019 | Banet ................ | A61B 5/02028 |
| 10,413,025 | B1 * | 9/2019 | Cwalinski ............ | A44C 15/005 |
| 10,750,795 | B1 * | 8/2020 | Lin ....................... | A44C 11/002 |
| 2002/0089859 | A1 * | 7/2002 | Jackson ............. | A44C 15/0015 |
| | | | | 362/571 |
| 2008/0287768 | A1 * | 11/2008 | Kuo ........................ | A61B 5/282 |
| | | | | 600/382 |
| 2016/0213508 | A1 * | 7/2016 | Sherman ............... | B65B 7/2821 |
| 2019/0373747 | A1 * | 12/2019 | Lin .......................... | H01Q 1/36 |

FOREIGN PATENT DOCUMENTS

| CN | 2768840 | 4/2006 |
| CN | 204796905 | 11/2015 |
| CN | 205125283 | 4/2016 |
| CN | 205432437 | 8/2016 |
| CN | 205512782 | 8/2016 |

(Continued)

*Primary Examiner* — Ahshik Kim
(74) *Attorney, Agent, or Firm* — JCIPRNET

(57) ABSTRACT

A wearable electronic device includes a plurality of secondary spheres and a main sphere connected in series. The main sphere includes a lower cover, an upper cover, a threading pillar, a chip, and a wireless transmitting component. The lower cover has a first assembling space. The upper cover is disposed on the lower cover and covers the first assembling space. The upper cover has a second assembling space communicated with the first assembling space. The threading pillar is clamped between the lower cover and the upper cover and is located in the first assembling space and the second assembling space. Both of the chip and the wireless transmitting component are disposed in the first assembling space, and the wireless transmitting component is electrically connected to the chip. An assembling method of a wearable electronic device is also provided.

17 Claims, 8 Drawing Sheets

(56) References Cited

FOREIGN PATENT DOCUMENTS

| | | |
|---|---|---|
| CN | 108720192 | 11/2018 |
| KR | 101596630 | 2/2016 |
| TW | I645688 | 12/2018 |
| TW | M572185 | 1/2019 |

* cited by examiner

WEARABLE ELECTRONIC DEVICE AND ASSEMBLING METHOD THEREOF

CROSS-REFERENCE TO RELATED APPLICATION

This application claims the priority benefit of Taiwan application serial no. 108126422, filed on Jul. 25, 2019. The entirety of the above-mentioned patent application is hereby incorporated by reference herein and made a part of this specification.

BACKGROUND OF THE INVENTION

1. Field of the Invention

The present invention relates to an electronic device, and particularly relates to a wearable electronic device.

2. Description of Related Art

Religious beliefs can give the public a sense of security and stability. In the case of Buddhism, users can wear a string of beads and pray by dialing the string of beads according to individual needs. With the development of the science and technology and the evolution of the times, a string of beads with an electronic operation function and a signal transmission function have been proposed to record the number of dialing and the number of praying, or to send the prayer text to a specified object through a cloud terminal. Therefore, the operation convenience of the users can be greatly improved, and the users can interact with other users.

The functions of the above string of beads are still mainly related to religious behaviors or religious rituals. Relevant manufacturers are all thinking about how to integrate functions related to daily behaviors, business behaviors or consumer behaviors and the like into the string of beads to enhance the functionality of the string of beads and increase the user dependence on the string of beads.

SUMMARY OF THE INVENTION

The present invention is directed to a wearable electronic device which integrates a mobile payment function.

The present invention is directed to an assembling method of a wearable electronic device, which is favorable for mass production and improves the product yield.

A wearable electronic device according to an embodiment of the present invention includes a plurality of secondary spheres and a main sphere. The main sphere is connected in series to the secondary spheres. An outer diameter of the main sphere is between 9 mm and 15 mm, and the main sphere includes a lower cover, an upper cover, a threading pillar, a chip and a wireless transmitting component. The lower cover has a first assembling space. The upper cover is disposed on the lower cover and covers the first assembling space. The upper cover has a second assembling space, and the first assembling space is communicated with the second assembling space. The threading pillar is clamped between the lower cover and the upper cover and is located in the first assembling space and the second assembling space. The chip is disposed in the first assembling space. The wireless transmitting component is disposed in the first assembling space and is electrically connected to the chip.

A wearable electronic device according to another embodiment of the present invention includes a plurality of secondary spheres and a main sphere. The main sphere is connected in series to the secondary spheres. An outer diameter of the main sphere is between 9 mm and 15 mm, and the main sphere includes a lower cover, an upper cover, a threading pillar, a chip holder, a chip, and a wireless transmitting component. The lower cover has a first assembling space. The upper cover is disposed on the lower cover and covers the first assembling space. The upper cover has a second assembling space, and the first assembling space is communicated with the second assembling space. The threading pillar is clamped between the lower cover and the upper cover and is located in the first assembling space and the second assembling space. The chip holder is connected to the threading pillar and is located in the second assembling space. The chip is disposed on the chip holder and is located in the second assembling space. The wireless transmitting component is disposed in the first assembling space and is electrically connected to the chip.

An assembling method of a wearable electronic device according to an embodiment of the present invention includes the following steps. Firstly, a lower cover having a first assembling space is provided. Next, a wireless transmitting component is electrically connected to a chip, and the wireless transmitting component and the chip are assembled in the first assembling space. A threading pillar is assembled on the lower cover. An upper cover having a second assembling space is provided. The upper cover is assembled on the lower cover to clamp the threading pillar between the lower cover and the upper cover. The upper cover covers the first assembling space, and the first assembling space is communicated with the second assembling space, and the threading pillar is located in the first assembling space and the second assembling space. A plurality of secondary spheres are connected in series to a main sphere manufactured according to the above steps.

An assembling method of a wearable electronic device according to another embodiment of the present invention includes the following steps. Firstly, a lower cover having a first assembling space is provided. Next, a threading pillar and a chip holder which are integrally formed are provided. A chip is assembled on the chip holder, and a wireless transmitting component is electrically connected to the chip. The wireless transmitting component is assembled in the first assembling space, and the threading pillar is assembled on the lower cover. An upper cover which has a second assembling space is provided. The upper cover is assembled on the lower cover to clamp the threading pillar between the lower cover and the upper cover. The upper cover covers the first assembling space, and the first assembling space is communicated with the second assembling space. The threading pillar is located in the first assembling space and the second assembling space, and the chip holder and the chip are located in the second assembling space. A plurality of secondary spheres are connected in series to a main sphere manufactured according to the above steps.

Based on the above, in the wearable electronic device provided by the present invention, the chip and the wireless transmitting component are integrated in the main sphere to execute a mobile payment function (especially an inductive payment function). On the other hand, the assembling method of the wearable electronic device provided by the present invention is simple and clear, is favorable for mass production, and can save the assembling time and improve the product yield.

In order to make the aforementioned and other objectives and advantages of the present invention comprehensible, embodiments accompanied with figures are described in detail below.

DESCRIPTION OF THE EMBODIMENTS

Figure 1:
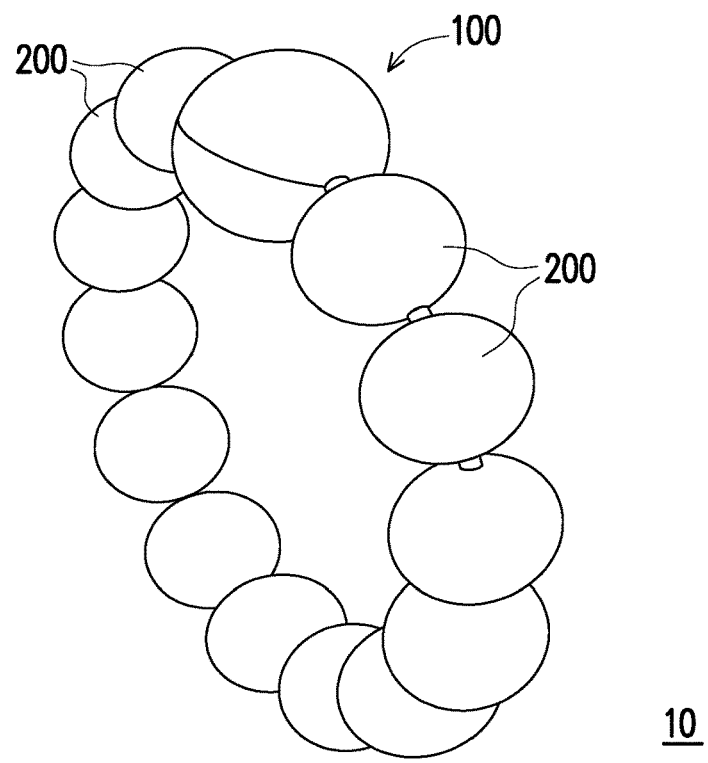
FIG. 1 is a schematic view of a wearable electronic device according to an embodiment of the present invention.
Figure 2:
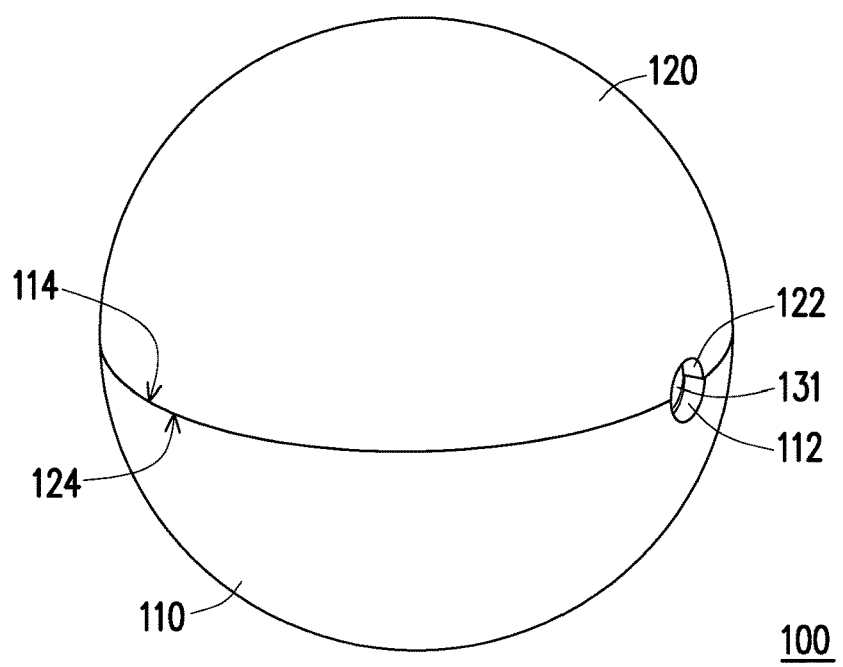
FIG. 2 is a schematic view of a main sphere according to an embodiment of the present invention.
Figure 3:
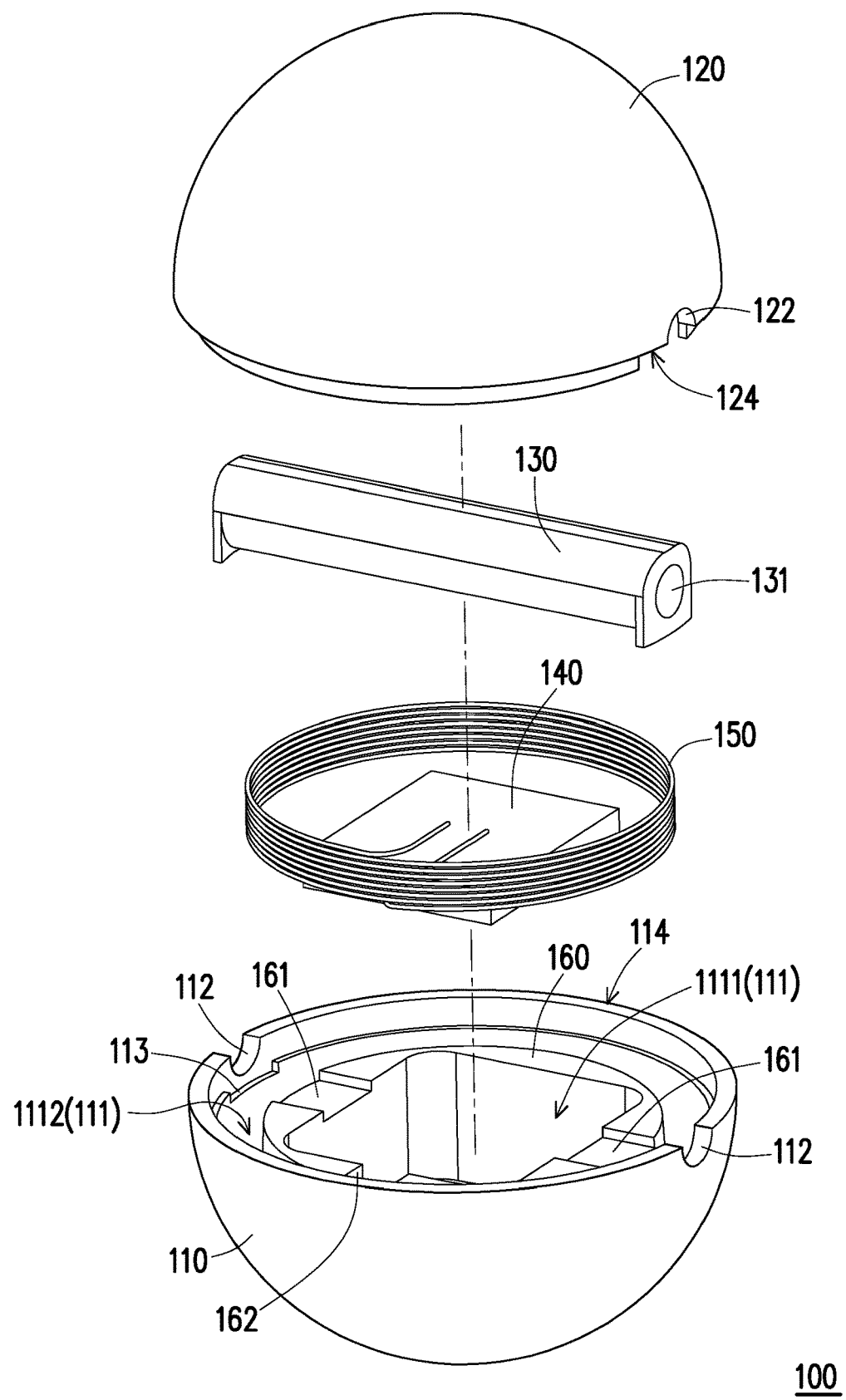
FIG. 3 is an explosive schematic view of the main sphere in FIG. 2.
Figure 4:
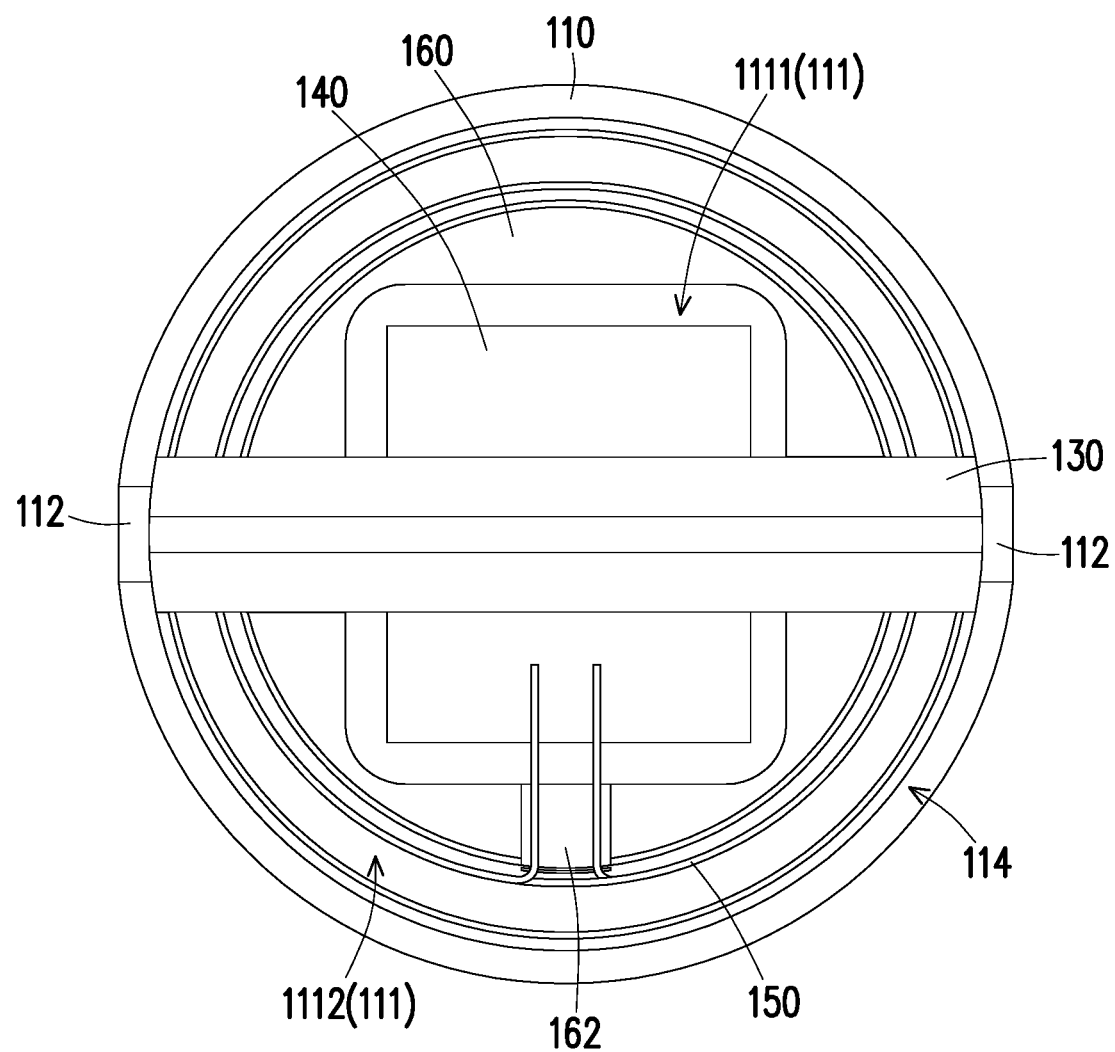
FIG. 4 is a top schematic view of the main sphere in FIG. 2 of which an upper cover is removed.
Figure 5:
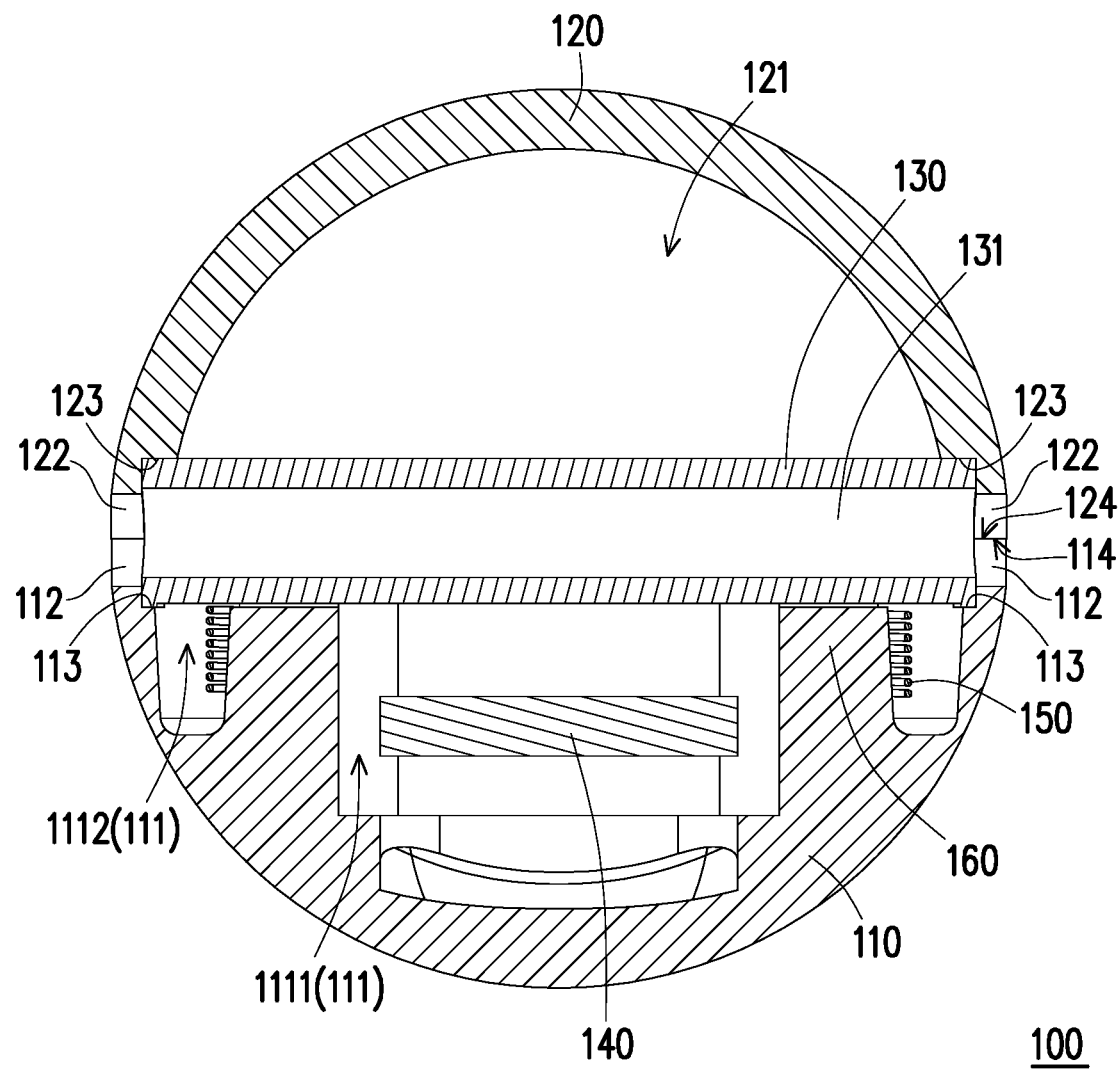
FIG. 5 is a cross-sectional schematic view of the main sphere in FIG. 2.

FIG. 1 is a schematic view of a wearable electronic device according to an embodiment of the present invention. FIG. 2 is a schematic view of a main sphere according to an embodiment of the present invention. FIG. 3 is an explosive schematic view of the main sphere in FIG. 2. FIG. 4 is a top schematic view of the main sphere in FIG. 2 of which an upper cover is removed. FIG. 5 is a cross-sectional schematic view of the main sphere in FIG. 2. Firstly, referring to FIG. 1, in the present embodiment, a wearable electronic device 10 may be a string of beads including a main sphere 100 and a plurality of secondary spheres 200 connected in series. Specifically, the main sphere 100 integrates an electronic operation function and a signal transmission function to record the number of dialing and the number of praying, or to send a prayer text to a specified object through a cloud terminal. The secondary spheres 200 may be solid spheres made of wood or plastic, but the secondary spheres 200 have threading holes for threading. In other embodiments, the secondary spheres 200 may also integrate an electronic operation function and a signal transmission function, but the present invention is not limited thereto.

Then, referring to FIG. 2, in the present embodiment, the main sphere 100 is a hollow sphere, so that required electronic components can be assembled inside the main sphere 100. Further, the main sphere 100 is composed of a lower cover 110 and an upper cover 120, and the lower cover 110 and the upper cover 120 may be two matched hollow hemispheres. Therefore, after the required electronic components are assembled inside the lower cover 110 or the upper cover 120, the lower cover 110 and the upper cover 120 are combined and fixed so as to complete an assembly process of the main sphere 100.

Referring to FIG. 2 to FIG. 5, in the present embodiment, a main sphere 100 includes a lower cover 110, an upper cover 120, a threading pillar 130, a chip 140, and a wireless transmitting component 150. The lower cover 110 has a first assembling space 111, and the upper cover 120 has a second assembling space 121 matched with the first assembling space 111. The upper cover 120 is arranged on the lower cover 110 and covers the first assembling space 111, and the first assembling space 111 is communicated with the second assembling space 121 to contain the threading pillar 130, the chip 140 and the wireless transmitting component 150.

The threading pillar 130 is used for reserving a threading channel of the main sphere 100, and the threading pillar 130 is clamped and fixed between the lower cover 110 and the upper cover 120. A part of the threading pillar 130 is located in the first assembling space 111, and the other part of the threading pillar 130 is located in the second assembling space 121. Specifically, the lower cover 110 also has first through holes 112 communicated with the first assembling space 111, and the upper cover 120 also has second through holes 122 communicated with the second assembling space 121. More specifically, the number of the first through holes 112 is two, and the two first through holes 112 are radially formed in two sides of the lower cover 110. On the other hand, the number of the second through holes 122 is two, and the two second through holes 122 are radially formed in two sides of the upper cover 120.

The first through holes 112 and the second through holes 122 may be semicircular holes, and each first through hole 112 is butted to a second through hole 122 to form a circular hole. On the other hand, the threading pillar 130 has threading holes 131, and two ends of the threading holes 131 are respectively aligned with two circular holes formed by the first through holes 112 and the second through holes 122 for threading. Specifically, the lower cover 110 also has first slots 113 located in the first assembling space 111, and the upper cover 120 also has second slots 123 located in the second assembling space 121. More specifically, the number of the first slots 113 is two, and the two first slots 113 are radially formed in two sides of the lower cover 110. The first slots 113 are adjacent to the first through holes 112, and each first through hole 112 and a first slot 113 form a group. The number of the second slots 123 is two, and the two second slots 123 are radially formed in two sides of the upper cover 120. The second slots 123 are adjacent to the second through holes 122, and each second through hole 122 and a second slot 123 form a group.

The first slots 113 and the second slots 123 can be used for locating the threading pillar 130 in the lower cover 110 and the upper cover 120, thereby preventing the threading pillar 130 from being offset from the lower cover 110 and the upper cover 120, and ensuring that the threading holes 131 of the threading pillar 130 are aligned with the two circular holes formed by the first through holes 112 and the second through holes 122. For example, a first slot 113 and a second slot 123 corresponding to a circular hole are aligned with each other and are used for clamping and fixing one end of the threading pillar 130. On the other hand, the other first slot 113 and the other second slot 123 corresponding to the other circular hole are aligned with each other and are used for clamping and fixing the other end of the threading pillar 130.

In the present embodiment, the chip 140 may have logical operation and data access functions and the like, and the wireless transmitting component 150 may be an antenna. The wireless transmitting component 150 and the chip 140 are electrically connected and are disposed in the first assembling space 111. Specifically, the lower cover 110 includes a chip holder 160 located in the first assembling space 111, and the chip holder 160 divides the first assembling space 111 into a first assembling groove 1111 and a second assembling groove 1112. The chip holder 160 is a protrusion protruding from the inner wall surface of the lower cover 110, and can be used not only for defining the assembling locations of the chip 140 and the wireless transmitting component 150 but also for carrying the threading pillar 130. As shown in FIG. 3, the top of the chip holder 160 has grooves 161 for locating the threading pillar 130.

Referring to FIG. 3 to FIG. 5, the second assembling groove 1112 surrounds the first assembling groove 1111, The chip 140 is disposed in the first assembling groove 1111, and the wireless transmitting component 150 is disposed in the second assembling groove 1112. On the other hand, the threading pillar 130 leans against the top of the chip holder 160 and crosses the first assembling groove 1111 and the second assembling groove 1112. In other words, the assembling locations of the threading pillar 130, the chip 140 and the wireless transmitting component 150 can be determined by the chip holder 160 to avoid structural interference of the threading pillar 130, the chip 140 and the wireless transmitting component 150. Furthermore, the chip holder 160 has a routing groove 162 communicated with the first assembling groove 1111 and the second assembling groove 1112, and a part of the wireless transmitting component 150 extends into the first assembling groove 1111 through the routing groove 162 to ensure the electrical connection relationship between the wireless transmitting component 150 and the chip 140.

In the present embodiment, the wireless transmitting component 150 can adopt a radio frequency identification (RFID) antenna or a near field communication (NFC) antenna to integrate a mobile payment function (especially an inductive payment function) to the main sphere 100. On the other hand, the antenna is of a helical structure, and an outer diameter of the main sphere 100 is between 9 mm and 15 mm. In order to construct the antenna in a limited internal space and enable the antenna to have sufficient inductance, the number of turns of the antenna is designed to be 16. In other words, under small-size design limitation, the antenna in the main sphere 100 still has an excellent induction effect for executing an inductive payment function.

An assembling method of the wearable electronic device 10 is described below.

Referring to FIG. 1, FIG. 2, FIG. 3 and FIG. 5, firstly, the lower cover 110 is provided. Then, the wireless transmitting component 150 is electrically connected to the chip 140, and the wireless transmitting component 150 and the chip 140 are synchronously assembled in the first assembling space 111. Specifically, the first assembling space 111 is divided into the first assembling groove 1111 and the second assembling groove 1112 surrounding the first assembling groove 1111 by the chip holder 160. In the process of synchronously assembling the wireless transmitting component 150 and the chip 140 in the first assembling space 111, the wireless transmitting component 150 is assembled in the second assembling groove 1112, and the chip 140 is assembled in the first assembling groove 1111. Furthermore, a part of the wireless transmitting component 150 must be aligned with and moved into the routing groove 162 to ensure the electrical connection relationship between the wireless transmitting component 150 and the chip 140.

Then, two ends of the threading pillar 130 are respectively aligned with and clamped into the first slots 113 to assemble and fix the threading pillar 130 on the lower cover 110. Then, the upper cover 120 is provided, and the second slots 123 of the upper cover 120 are respectively aligned with the first slots 113 and two ends of the threading pillar 130. Then, the upper cover 120 is assembled on the lower cover 110, and two ends of the threading pillar 130 are respectively aligned with and clamped into the second slots 123 to clamp and fix the threading pillar 130 between the lower cover 110 and the upper cover 120.

The lower cover 110 has a first assembling surface 114 surrounding the first assembling space 111, and the upper cover 120 has a second assembling surface 124 surrounding the second assembling space 121. For example, at least one of the first assembling surface 114 and the second assembling surface 124 is provided with adhesive, after the upper cover 120 is assembled on the lower cover 110, the second assembling surface 124 abuts against the first assembling surface 114, and the upper cover 120 and the lower cover 110 are fixed via the adhesive. On the other hand, the upper cover 120 covers the first assembling space 111. The first assembling space 111 is communicated with the second assembling space 121, and the threading pillar 130 is located in the first assembling space 111 and the second assembling space 121. So far, the assembly process of the main sphere 100 is substantially completed. Finally, the assembled main sphere 100 and a plurality of secondary spheres 200 are connected in series to complete the assembly process of the wearable electronic device 10.

The assembling method of the wearable electronic device 10 is favorable for mass production and can save the assembling time and improve the product yield.

Figure 6:
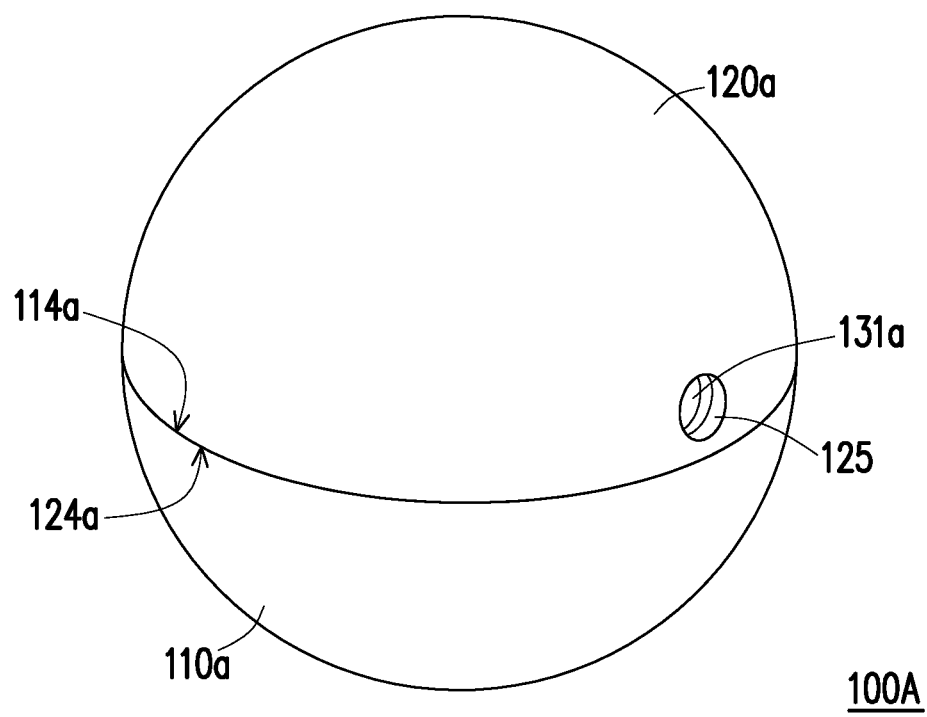
FIG. 6 is a schematic view of a main sphere according to another embodiment of the present invention.
Figure 7:
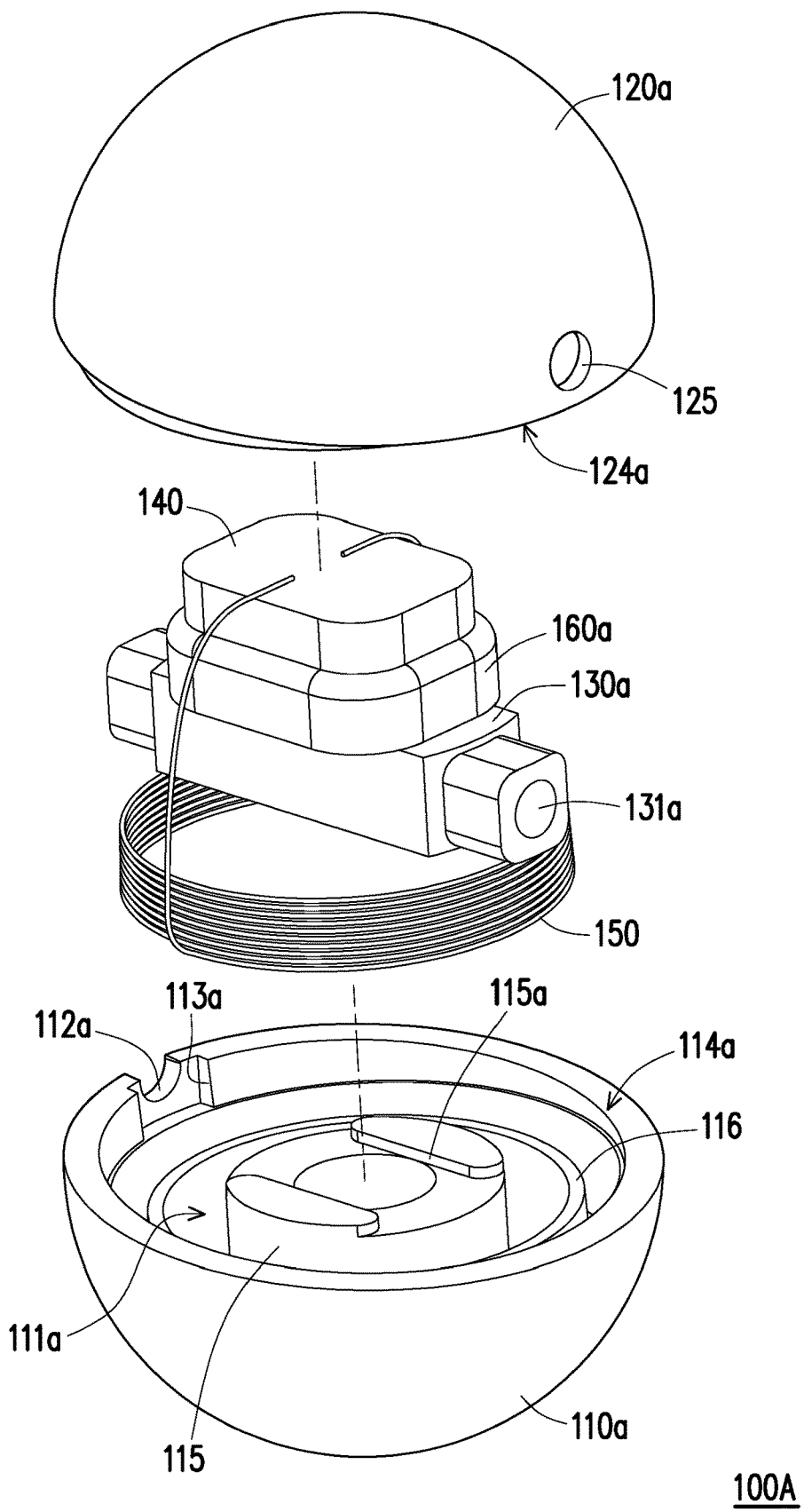
FIG. 7 is an explosive schematic view of the main sphere in FIG. 6.
Figure 8:
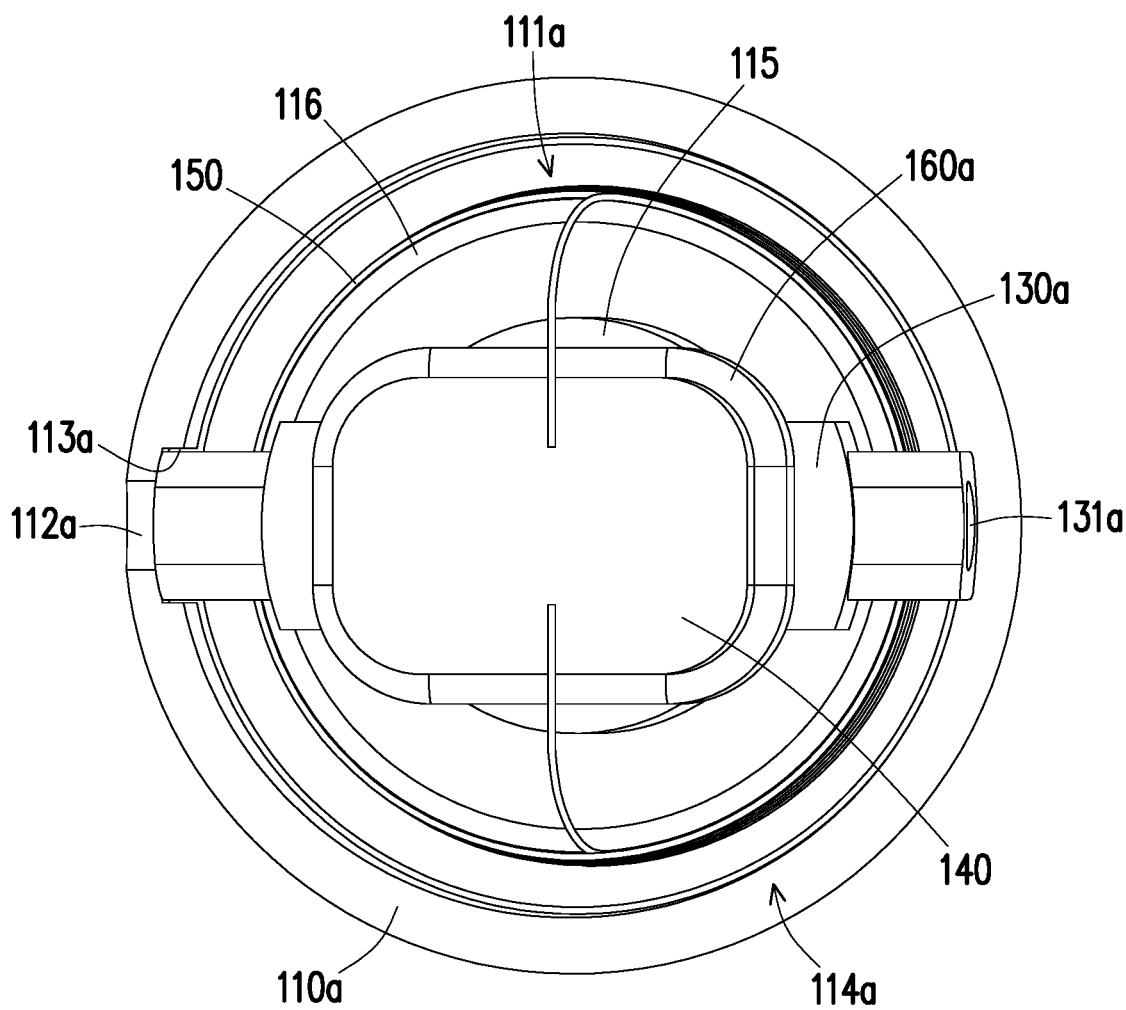
FIG. 8 is a top schematic view of the main sphere in FIG. 6 of which an upper cover is removed.
Figure 9:
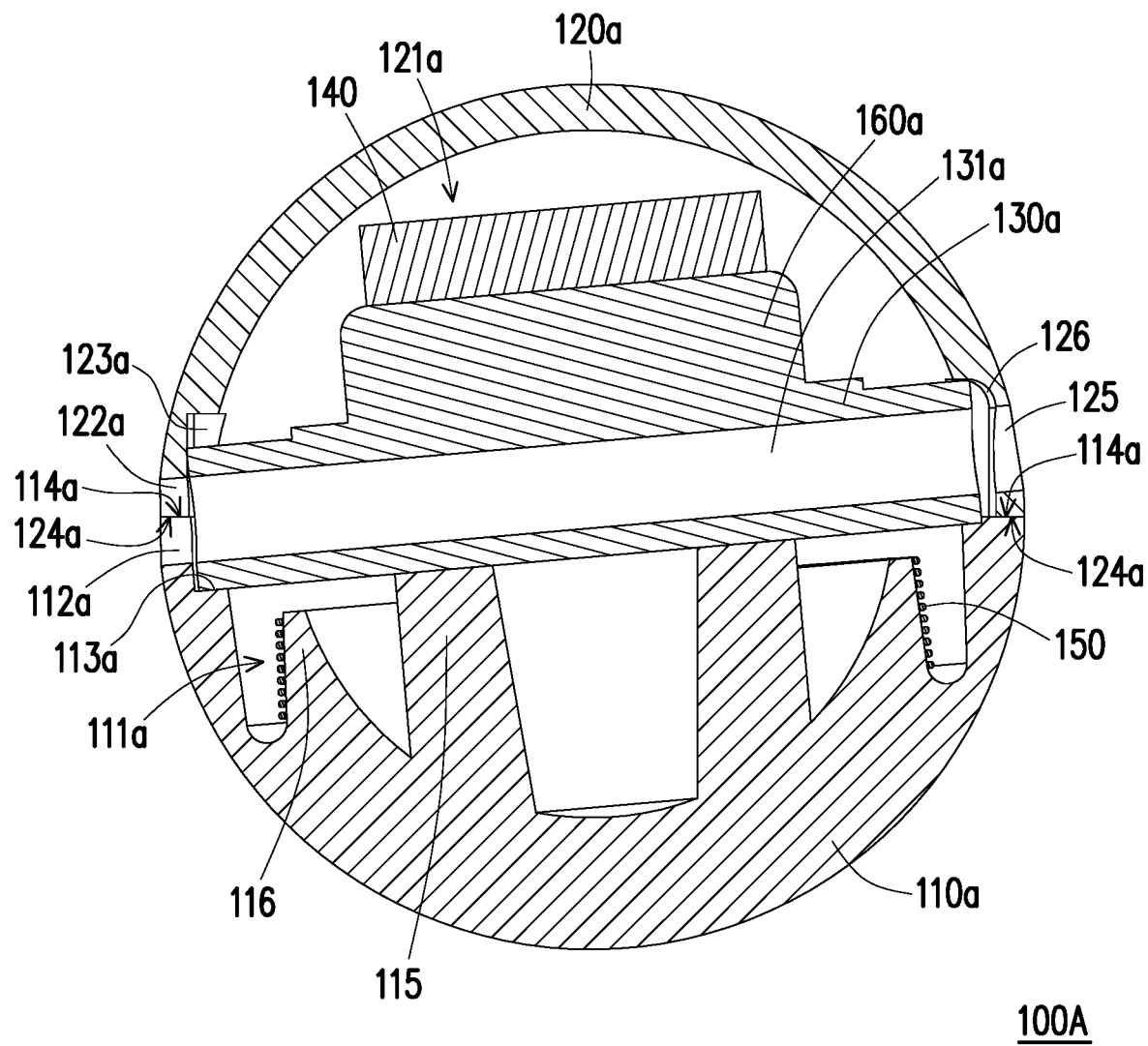
FIG. 9 is a cross-sectional schematic view of the main sphere in FIG. 6.

FIG. 6 is a schematic view of a main sphere according to another embodiment of the present invention. FIG. 7 is an explosive schematic view of the main sphere in FIG. 6. FIG. 8 is a top schematic view of the main sphere in FIG. 6 of which an upper cover is removed. FIG. 9 is a cross-sectional schematic view of the main sphere in FIG. 6. Firstly, referring to FIG. 6, the main sphere 100 in the wearable electronic device 10 according to the previous embodiment can be replaced with a main sphere 100A according to the present embodiment. In other words, the main sphere 100A can be connected in series to a plurality of secondary spheres 200 as shown in FIG. 1 to form a wearable electronic device according to another embodiment.

The difference between the main sphere 100A and the main sphere 100 according to the previous embodiment is described below, and the descriptions of the same or similar parts are not repeated.

Referring to FIG. 6 to FIG. 9, in the present embodiment, the main sphere 100A includes a lower cover 110a, an upper cover 120a, a threading pillar 130a, a chip 140, a wireless transmitting component 150, and a chip holder 160a. The lower cover 110a has a first assembling space 111a, and the upper cover 120a has a second assembling space 121a matched with the first assembling space 111a. The upper cover 120a is disposed on the lower cover 110a and covers the first assembling space 111a, and the first assembling space 111a is communicated with the second assembling space 121a to contain the threading pillar 130a, the chip 140, the wireless transmitting component 150 and the chip holder 160a.

The threading pillar 130a and the chip holder 160a may be of an integrally formed structure and may be manufactured by adopting an injection molding technology. The threading pillar 130a is used for reserving a threading channel of the main sphere 100A, and the threading pillar 130a is clamped and fixed between the lower cover 110a and the upper cover 120a. A part of the threading pillar 130a is located in the first assembling space 111a, and the other part of the threading pillar 130a is located in the second assembling space 121a. On the other hand, the chip holder 160a is used for carrying the chip 140, and the chip holder 160a and the chip 140 fixed on the chip holder 160a are located in the second assembling space 121a. The wireless transmitting component 150 is electrically connected to the chip 140, and the wireless transmitting component 150 is disposed in the first assembling space 111a.

Specifically, the lower cover 110a also has first through holes 112a communicated with the first assembling space 111a, and the upper cover 120a also has second through holes 122a communicated with the second assembling space 121a. Each first through hole 112a is butted to a second through hole 122a to form a circular hole, and one end of a threading hole 131a of the threading pillar 130a is aligned with the circular hole for threading. The lower cover 110a also has first slots 113a located in the first assembling space 111a, and the upper cover 120 also has second slots 123a located in the second assembling space 121a. The first slots 113a are adjacent to the first through holes 112a, and each first through hole 112a and a first slot 113a form a group. The second slots 123a are adjacent to the second through holes 122a, and each second through hole 122a and a second slot 123a form a group.

The first slots 113a and the second slots 123a are aligned with each other and can be used for locating the threading pillar 130a in the lower cover 110a and the upper cover 120a. One end of the threading pillar 130a is clamped and fixed in the first slots 113a and the second slots 123a. The first slots 113a and the second slots 123a can prevent the threading pillar 130a from being offset from the lower cover 110a and the upper cover 120a, and can ensure that one ends of the threading holes 131a of the threading pillar 130a are aligned with the circular holes formed by the first through holes 112a and the second through holes 122a. On the other hand, the upper cover 120a also has through holes 125 communicated with the second assembling space 121a, and the other ends of the threading holes 131a of the threading pillar 130a are aligned with the through holes 125 for threading. Further, the upper cover 120a also has slots 126 located in the second assembling space 121a. The slots 126 are adjacent to the through holes 125, and each slot 126 and a through hole 125 form a group. The slots 126 can be used for locating the threading pillar 130a in the upper cover 120a. The other end of the threading pillar 130a is clamped and fixed in the slots 126. The slots 126 can prevent the threading pillar 130a from being offset from the upper cover 120a, and can ensure that the other ends of the threading holes 131a of the threading pillar 130a are aligned with the through holes 125.

Based on the above, the through holes 125 and the circular holes formed by the first through holes 112a and the second through holes 122a are asymmetrically designed, so that the threading pillar 130a clamped and fixed between the lower cover 110a and the upper cover 120a has an inclination angle. Correspondingly, the chip holder 160a which is integrally formed on the threading pillar 130a and the chip 140 which is fixed on the chip holder 160a also have an inclination angle. Further, the first through holes 112a penetrate through the first assembling surface 114a of the lower cover 110a, and the second through holes 122a penetrate through the second assembling surface 124a of the upper cover 120a. Furthermore, the through holes 125 are formed in the outer wall surface of the upper cover 120a and do not penetrate through the second assembling surface 124a. The second assembling surface 124a abuts against the first assembling surface 114a. Two ends of the threading holes 131a of the threading pillar 130a are respectively aligned with the through holes 125 and the circular holes formed by the first through holes 112a and the second through holes 122a, and connecting lines between the through holes 125 and the circular holes formed by the first through holes 112a and the second through holes 122a incline to the second assembling surface 124a and the first assembling surface 114a. Correspondingly, the threading pillar 130a also inclines to the second assembling surface 124a and the first assembling surface 114a.

In the present embodiment, the lower cover 110a includes a carrying part 115 located in the first assembling space 111a and a locating part 116 surrounding the carrying part 115. The carrying part 115 is a convex pillar protruding from the inner wall surface of the lower cover 110a, and the locating part 116 is a convex ring protruding from the inner wall surface of the lower cover 110a. The threading pillar 130a leans against the carrying part 115. The antenna (wireless transmitting component 150) surrounds the locating part 116, and the locating part 116 is located between the carrying part 115 and the antenna (wireless transmitting component 150). The threading pillar 130a crosses above the locating part 116, so that the antenna (wireless transmitting component 150) and the threading pillar 130a cannot generate structural interference. On the other hand, the top of the carrying part 115 has a groove 115a for locating the threading pillar 130a.

An assembling method of the main sphere 100A is described below.

Referring to FIG. 6, FIG. 7 and FIG. 9, firstly, the lower cover 110a is provided. Then, the threading pillar 130a and the chip holder 160a which are integrally formed are provided. Then, the chip 140 is fixed on the chip holder 160a, and the wireless transmitting component 150 is electrically connected to the chip 140. Then, the wireless transmitting component 150 is assembled in the first assembling space 111a, and one end of the threading pillar 130a is aligned with and clamped into the first slots 113a to assemble and fix the threading pillar 130a on the lower cover 110a. At this time, the other end of the threading pillar 130a leans against the lower cover 110a. After the threading pillar 130a is assembled and fixed on the lower cover 110a, the chip holder 160a and the chip 140 fixed on the chip holder 160a are located outside the first assembling space 111a.

Then, the upper cover 120a is provided, and the second slots 123a of the upper cover 120a are aligned with the first slots 113 and one end of the threading pillar 130a. Simultaneously, the slots 126 are aligned with the other end of the threading pillar 130a. Then, the upper cover 120a is assembled on the lower cover 110a, and two ends of the threading pillar 130a are respectively aligned with and clamped into the second slots 123 and the slots 126 to clamp and fix the threading pillar 130a between the lower cover 110a and the upper cover 120a.

At least one of the first assembling surface 114a of the lower cover 110a and the second assembling surface 124a of the upper cover 120a is provided with adhesive, and after the upper cover 120a is assembled on the lower cover 110a, the second assembling surface 124a abuts against the first assembling surface 114a, and the upper cover 120a and the lower cover 110a are fixed through the adhesive. On the other hand, the upper cover 120a covers the first assembling space 111a. The first assembling space 111a is communicated with the second assembling space 121a, and the threading pillar 130a is located in the first assembling space 111a and the second assembling space 121a. The chip holder 160a and the chip 140 are located in the second assembling space 121a.

So far, the assembly process of the main sphere 100A is substantially completed.

Finally, the assembled main sphere 100A and a plurality of secondary spheres 200 as shown in FIG. 1 are connected in series to form the wearable electronic device according to another embodiment.

Based on the above, in the wearable electronic device provided by the present invention, the chip and the wireless transmitting component are integrated in the main sphere to execute a mobile payment function (especially an inductive payment function). Specifically, the wireless transmitting component can adopt an RFID antenna or an NFC antenna, and the outer diameter of the main sphere is between 9 mm and 15 mm. Under small-size design limitation, the number of turns of the antenna is designed to be 16, so that the antenna in the main sphere still has an excellent induction effect. On the other hand, the assembling method of the wearable electronic device provided by the present invention is simple and clear, is favorable for mass production, and can save the assembling time and improve the product yield.

Although the invention is described with reference to the above embodiments, the embodiments are not intended to limit the invention. A person of ordinary skill in the art may make variations and modifications without departing from the spirit and scope of the invention. Therefore, the protection scope of the invention should be subject to the appended claims.

What is claimed is:

1. A wearable electronic device, comprising:
   a plurality of secondary spheres; and
   a main sphere connected in series to the secondary spheres, wherein an outer diameter of the main sphere is between 9 mm and 15 mm, and the main sphere comprises:
   a lower cover having a first assembling space;
   an upper cover disposed on the lower cover and covering the first assembling space, wherein the upper cover has a second assembling space, and the first assembling space is communicated with the second assembling space;
   a threading pillar clamped between the lower cover and the upper cover and located in the first assembling space and the second assembling space;
   a chip disposed in the first assembling space; and
   a wireless transmitting component disposed in the first assembling space and electrically connected to the chip, wherein the wireless transmitting component is a coil antenna to execute an inductive payment function.

2. The wearable electronic device according to claim 1, wherein the lower cover has first through holes communicated with the first assembling space, the upper cover has second through holes communicated with the second assembling space, and the first through holes are butted to the second through holes, wherein the threading pillar has threading holes, and the threading holes are aligned with the first through holes and the second through holes.

3. The wearable electronic device according to claim 2, wherein the lower cover also has first slots located in the first assembling space, the upper cover also has second slots located in the second assembling space, the first slots are adjacent to the first through holes, the second slots are adjacent to the second through holes, the first slots are aligned with the second slots, and the threading pillar is clamped in the first slots and the second slots.

4. The wearable electronic device according to claim 1, wherein the lower cover comprises a chip holder located in the first assembling space, the chip holder divides the first assembling space into a first assembling groove and a second assembling groove, the chip is arranged in the first assembling groove, and the wireless transmitting component is disposed in the second assembling groove.

5. The wearable electronic device according to claim 4, wherein the threading pillar leans against the chip holder and crosses the first assembling groove and the second assembling groove.

6. The wearable electronic device according to claim 4, wherein the second assembling groove surrounds the first assembling groove, the chip holder has a routing groove communicated with the first assembling groove and the second assembling groove, and a part of the wireless transmitting component extends into the first assembling groove through the routing groove.

7. The wearable electronic device according to claim 1, wherein the wireless transmitting component is an antenna.

8. A wearable electronic device, comprising:
   a plurality of secondary spheres; and
   a main sphere connected in series to the secondary spheres, wherein an outer diameter of the main sphere is between 9 mm and 15 mm, and the main sphere comprises:
   a lower cover having a first assembling space;
   an upper cover disposed on the lower cover and covering the first assembling space, wherein the upper cover has a second assembling space, and the first assembling space is communicated with the second assembling space;
   a threading pillar clamped between the lower cover and the upper cover and located in the first assembling space and the second assembling space;
   a chip holder connected to the threading pillar and located in the second assembling space;
   a chip disposed on the chip holder and located in the second assembling space; and
   a wireless transmitting component disposed in the first assembling space and electrically connected to the chip.

9. The wearable electronic device according to claim 8, wherein the lower cover also has first through holes communicated with the first assembling space, the upper cover also has second through holes communicated with the second assembling space, and the first through holes are butted to the second through holes, wherein the threading pillar has threading holes, and the threading holes are aligned with the first through holes and the second through holes.

10. The wearable electronic device according to claim 9, wherein the lower cover also has first slots located in the first assembling space, the upper cover also has second slots located in the second assembling space, the first slots are adjacent to the first through holes, the second slots are adjacent to the second through holes, the first slots are aligned with the second slots, and the threading pillar is clamped in the first slots and the second slots.

11. The wearable electronic device according to claim 8, wherein the upper cover also has through holes communicated with the second assembling space, the threading pillar has threading holes, and the threading holes are aligned with the through holes.

12. The wearable electronic device according to claim 11, wherein the upper cover also has slots located in the second assembling space, the slots are adjacent to the through holes, and the threading pillar is clamped in the slots.

13. The wearable electronic device according to claim 8, wherein the lower cover comprises a carrying part located in the first assembling space and a locating part surrounding the carrying part, and the threading pillar leans against the carrying part.

14. The wearable electronic device according to claim 13, wherein the wireless transmitting component is an antenna, the antenna surrounds the locating part, and the locating part is located between the carrying part and the antenna.

15. The wearable electronic device according to claim 8, wherein the lower cover also has a first assembling surface, the upper cover also has a second assembling surface, and the second assembling surface abuts against the first assembling surface, and the threading pillar inclines to the first assembling surface and the second assembling surface.

16. An assembling method of a wearable electronic device, comprising:
- providing a lower cover, the lower cover having a first assembling space;
- enabling a wireless transmitting component to be electrically connected to a chip and assembling the wireless transmitting component and the chip in the first assembling space, wherein the wireless transmitting component is a coil antenna to execute an inductive payment function;
- assembling a threading pillar on the lower cover;
- providing an upper cover, the upper cover having a second assembling space;
- assembling the upper cover on the lower cover to clamp the threading pillar between the lower cover and the upper cover, the upper cover covering the first assembling space, wherein the first assembling space is communicated with the second assembling space, and the threading pillar is located in the first assembling space and the second assembling space; and
- connecting a plurality of secondary spheres in series to a main sphere manufactured according to the above steps.

17. An assembling method of a wearable electronic device, comprising:
- providing a lower cover, the lower cover having a first assembling space;
- providing a threading pillar and a chip holder which are integrally formed;
- assembling the chip on the chip holder and enabling the wireless transmitting component to be electrically connected to the chip;
- assembling the wireless transmitting component in the first assembling space and assembling the threading pillar on the lower cover;
- providing an upper cover, the upper cover having a second assembling space;
- assembling the upper cover on the lower cover to clamp the threading pillar between the lower cover and the upper cover, the upper cover covering the first assembling space, wherein the first assembling space is communicated with the second assembling space, the threading pillar is located in the first assembling space and the second assembling space, and the chip holder and the chip are located in the second assembling space; and
- connecting a plurality of secondary spheres in series to a main sphere manufactured according to the above steps.

* * * * *